(12) United States Patent
Beulke

(10) Patent No.: US 8,308,750 B2
(45) Date of Patent: Nov. 13, 2012

(54) REMOVABLE INTRAVASCULAR DEVICES AND METHODS OF MAKING AND USING THE SAME

(75) Inventor: Mel R. Beulke, Bloomington, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 2084 days.

(21) Appl. No.: 10/797,879

(22) Filed: Mar. 10, 2004

(65) Prior Publication Data

US 2005/0203566 A1 Sep. 15, 2005

(51) Int. Cl.
*A61M 29/00* (2006.01)

(52) U.S. Cl. .................................... 606/200

(58) Field of Classification Search .......... 606/200, 606/158, 159, 194, 195; 623/1.11, 1.23, 623/1.36

See application file for complete search history.

(56) References Cited

U.S. PATENT DOCUMENTS

| | | | |
|---|---|---|---|
| 4,425,908 A | 1/1984 | Simon | |
| 4,688,553 A | 8/1987 | Metals | |
| 4,781,177 A * | 11/1988 | Lebigot | 128/897 |
| 4,817,600 A | 4/1989 | Herms et al. | |
| 4,957,501 A | 9/1990 | Lahille et al. | |
| 4,969,891 A | 11/1990 | Gewertz | |
| 4,990,156 A * | 2/1991 | Lefebvre | 606/200 |
| 5,059,205 A | 10/1991 | El-Nounou et al. | |
| 5,071,407 A | 12/1991 | Termin et al. | |
| 5,108,418 A * | 4/1992 | Lefebvre | 606/200 |
| 5,108,419 A * | 4/1992 | Reger et al. | 606/200 |
| 5,133,733 A | 7/1992 | Rasmussen et al. | |
| 5,152,777 A | 10/1992 | Goldberg et al. | |
| 5,160,342 A | 11/1992 | Reger et al. | |
| 5,211,651 A | 5/1993 | Reger et al. | |
| 5,221,261 A | 6/1993 | Termin et al. | |
| 5,300,086 A | 4/1994 | Gory et al. | |
| 5,329,942 A | 7/1994 | Gunther et al. | |
| 5,344,427 A | 9/1994 | Cottenceau et al. | |
| 5,370,657 A | 12/1994 | Irie | |
| 5,397,345 A * | 3/1995 | Lazarus | 128/898 |
| 5,549,626 A | 8/1996 | Miller et al. | |
| 5,634,942 A * | 6/1997 | Chevillon et al. | 623/1.1 |
| 5,792,155 A | 8/1998 | Van Cleef et al. | |
| 5,827,324 A | 10/1998 | Cassell et al. | |
| 5,836,969 A | 11/1998 | Kim et al. | |
| 5,853,420 A * | 12/1998 | Chevillon et al. | 606/200 |
| 5,893,869 A | 4/1999 | Barnhart et al. | |
| 5,984,947 A | 11/1999 | Smith et al. | |
| 6,126,673 A | 10/2000 | Kim et al. | |
| 6,168,579 B1 | 1/2001 | Tsugita | |
| 6,171,328 B1 | 1/2001 | Addis | |
| 6,179,859 B1 | 1/2001 | Bates et al. | |

(Continued)

FOREIGN PATENT DOCUMENTS

WO WO 01/60442 A1 8/2001

(Continued)

*Primary Examiner* — Darwin Erezo

(74) *Attorney, Agent, or Firm* — Seager, Tufte & Wickhem LLC

(57) ABSTRACT

An intravascular device, which may be a filter, that may include a plurality of elongate members, each or several of the elongate members may have one or more inwardly facing edges disposed at and near the part of the intravascular device configured to contact the vessel wall for cutting through the intima or other encapsulating tissue, each of the elongate member may also include an anchoring member or other desired components.

21 Claims, 4 Drawing Sheets

U.S. PATENT DOCUMENTS

| | | |
|---|---|---|
| 6,193,739 B1 | 2/2001 | Chevillon et al. |
| 6,309,399 B1 * | 10/2001 | Barbut et al. ............ 606/159 |
| 6,391,045 B1 | 5/2002 | Kim et al. |
| 6,436,120 B1 | 8/2002 | Meglin |
| 6,436,121 B1 | 8/2002 | Blom |
| 6,443,971 B1 | 9/2002 | Boylan et al. |
| 6,443,972 B1 | 9/2002 | Bosma et al. |
| 6,482,222 B1 | 11/2002 | Bruckheimer et al. |
| 6,485,501 B1 | 11/2002 | Green |
| 6,491,698 B1 | 12/2002 | Bates et al. |
| 6,511,496 B1 | 1/2003 | Huter et al. |
| 6,511,503 B1 | 1/2003 | Burkett et al. |
| 6,540,767 B1 * | 4/2003 | Walak et al. ............ 606/200 |
| 6,582,447 B1 | 6/2003 | Patel et al. |
| 6,589,266 B2 | 7/2003 | Whitcher et al. |

FOREIGN PATENT DOCUMENTS

| | | |
|---|---|---|
| WO | WO 01/62184 A2 | 8/2001 |
| WO | WO 02/069845 A2 | 9/2002 |
| WO | WO 02/069845 A3 | 9/2002 |
| WO | WO 02/089869 A2 | 11/2002 |

* cited by examiner

REMOVABLE INTRAVASCULAR DEVICES AND METHODS OF MAKING AND USING THE SAME

FIELD

This invention relates to intravascular devises and particularly to intravascular devices which may be installed and may optionally be subsequently removed.

BACKGROUND

Certain intravascular devices may be left in a body lumen such as a blood vessel for a period of time. For example, a vena cava filter may be implanted in the vena cava to capture blood clots and other embolic debris and to retain the blood clots and other embolic debris while they are lysed or until removed. It may be desirable to leave this filter in place for a period of time such as two or more weeks after an interventional procedure, and then to remove the filter. These filters are often retained in place by means of elongate members which contact the vessel wall. The vessel wall frequently encapsulates the portion of the elongate members which contact the wall with endothelial growth. Thus, if removal is desired, it becomes necessary to free the elongate members from this endothelial growth.

SUMMARY

One embodiment pertains to a filter which can be removed from a vessel that has partially encapsulated it with minimal trauma to the vessel. The filter of this embodiment is a Greenfield style filter, though other filter configurations and other medical devices are contemplated. The filter has one or more elongate members configured to anchor to a vessel wall. Each elongate member has a first end and a second end. Attached to the second end may be an anchoring member for securing the filter to the vessel wall. Extending along the elongate member from the second end is a cutting edge. The cutting edge is directed towards a central elongate axis of the filter and consequently away from the nearest vessel wall.

A second embodiment pertains to a filter having one or more elongate members with an inward facing cutting edge similar to the first embodiment. The filter includes an inward facing cutting edge on a portion of the elongate member which has a reduced profile, so that the overall profile of that portion of the elongate member, including the cutting edge, is no greater than that of another portion of the elongate member.

Another embodiment pertains to a filter having one or more elongate members similar to the first embodiment. Provided on these elongate members are two or more cutting edges which may be generally aligned and facing inwards. These two or more cutting edges may be spaced apart from each other, providing gaps therebetween.

Yet another embodiment pertains to a filter having one or more elongate members similar to the first embodiment. At the end of each of the elongate members is a anchoring member comprising a hook, as will be described in more detail below. On the portion of the hook that is generally parallel to the elongate member is another cutting edge facing generally inwards.

Yet another embodiment pertains to a method of manufacture. A filter having elongate members is provided. A portion of the elongate members is worked to form an inward facing cutting edge. This may be done, for example, by electron discharge machining (EDM), by grinding, or by some other suitable process.

Yet another embodiment pertains to a second method of manufacture. A filter having elongate members is provided. A blade having a cutting edge is attached to an elongate member. This may be done, for example, by laser welding. Additionally or alternatively, a slot may be formed in the elongate member and a cutting blade is partially inserted into the slot, leaving an inward facing cutting edge exposed.

Yet another embodiment pertains to a method of use. A medical device having elongate members such as a vena cava filter is implanted in the vena cava, for example. The elongate members retain the medical device in place and have inward facing cutting edges disposed thereon. After a period, endothelial growth may partially encapsulate the elongate members in a process called neointimal hyperplasia. If removal is desired, the elongate members may be urged radially inward, causing the cutting edges to cut through the endothelial encapsulation. This defined cutting will be less traumatic compared to removal of an embodiment which lacks cutting edges and therefore must tear through any endothelial encapsulation. The retrieval force needed will likely be less. The medical device can then be compressed and removed from the vena cava.

The above summary of some embodiments is not intended to describe each disclosed embodiment or every implementation of the present invention. The figures and detailed description which follow more particularly exemplify these embodiments.

BRIEF DESCRIPTION OF THE DRAWINGS

The invention may be more completely understood in consideration of the following detailed description of various embodiments of the invention in connection with the accompanying drawings in which.

DETAILED DESCRIPTION OF SELECTED EMBODIMENTS

The following detailed description should be read with reference to the drawings, in which like elements in different drawings are numbered identically. The drawings which are not necessarily to scale, depict selected embodiments and are not intended to limit the scope of the invention.

Figure 1:
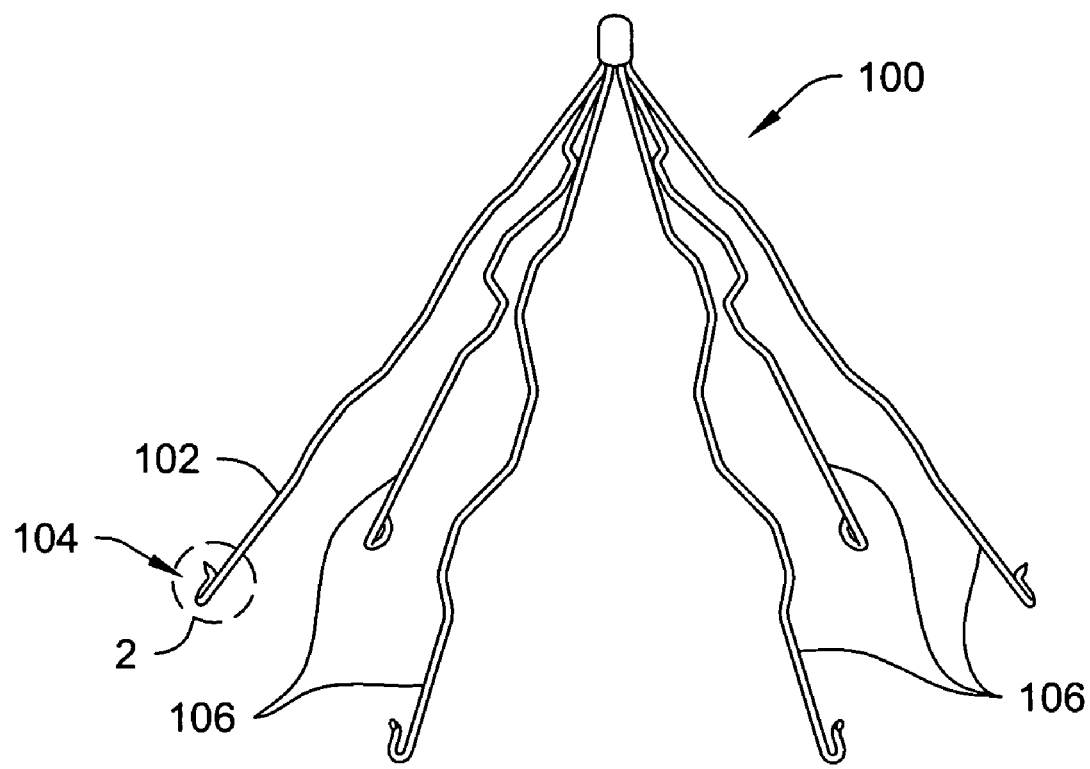
FIG. 1 is a perspective view of a vena cava filter according to the invention.

FIG. 1 is a perspective view of a vena cava filter 100 having an elongate member 102. Elongate member 102 may include an anchoring member 104 disposed on the end. Detailed reference is made to elongate member 102, but filter 100 may include additional elongate members 106, which may be configured substantially like elongate member 102. Filter 100 is selected to illustrate this embodiment, but neither this embodiment or any embodiment is limited to Filter 100. Other applications are contemplated. For example, the embodiment may be readily adapted to other vena cava filters. Indeed, the embodiment may be readily adapted to any implantable medical device retained in position by elongate members. Likewise, neither this embodiment or any embodiment is limited to medical devices retained by generally straight elongate members where an end of the elongate members is in contact with the vessel wall. Embodiments are contemplated where the elongate member contacts a vessel wall with a middle portion rather than an extremity. Such an elongate member may be, for example, curved. Embodiments, therefore, are contemplated with a wide variety of medical devices of numerous configurations.

In the present embodiment, elongate member 102 may be made from stainless steel or other suitable biocompatible materials such as nickel-titanium alloys. Elongate member 102 has a generally circular cross-section. Other suitable cross-sections are contemplated. For example, elliptical or rectangular may be equally or more suitable in certain applications. Elongate member 102 may be, if desired coated with therapeutic agents. For example, elongate member 102 may be coated with an agent to resist neointimal hyperplasia.

Figure 2:
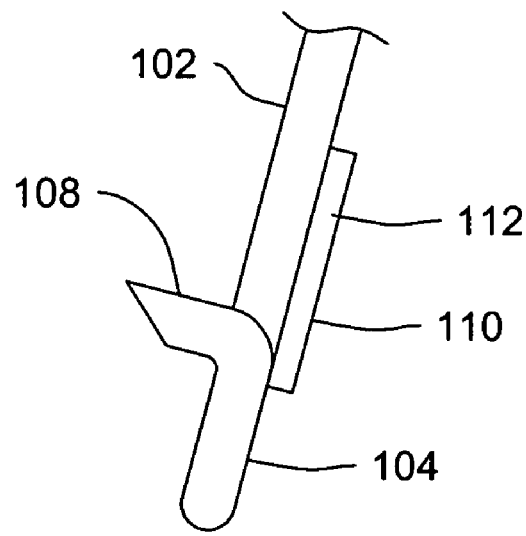
FIG. 2 is a side view of a strut of the filter of FIG. 1.

Refer now to FIG. 2, which is an enlarged side view of an end of elongate member 102. Anchor member 104 can be seen in greater detail. Anchor member 104 has a hook shape with a barb 108 disposed on the end. The hook shape and barb 108 may be used to retain filter 100 in a desired position. Disposed on elongate member 102 is an edge 110. Edge 110 generally faces in towards the center of filter 100 and away from the vessel wall. Edge 110 may be disposed on a blade 112 or may be a shaped part of elongate member 102. For example, edge 110 may be formed by electron deposition machining elongate member 102. Edge 110 may start near the hook end of elongate member 102 and extend up a portion of elongate member 102. In one embodiment, edge 110 extends sufficiently up elongate member 102 so that a portion of edge 110 has little chance of being encapsulated by a neointimal hyperplasia process. In other words, edge 110 may extend far enough away from the vessel wall and up elongate member 102 to keep exposed. Edge 110 should be sharp enough to cut through vessel growth.

Figure 3:
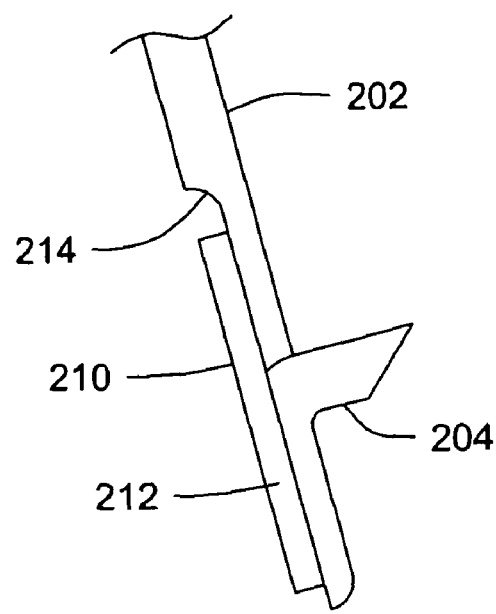
FIG. 3 is a side view of an elongate member of an intravascular device according to the invention.

FIG. 3 is a side view of an elongate member 202 of an intravascular device of another embodiment. Elongate member 202 may be part of a vena cava filter or may be part of another intravascular device. Elongate member may include an anchor member 204 and includes an edge 210. Edge 210 is disposed in a cut-out 214 of elongate member 204 and may be on a blade 212. The cut-out serves to reduce the overall cross section of the elongate member with the blade. In one embodiment, cut-out 214 is of sufficient depth so that the cross-section of the portion of elongate member 202 with edge 210 does not extend beyond the portion of elongate member 202 without a cut-out. Thus, the intravascular device may have a reduced profile when compressed for insertion or extraction.

Figure 4:
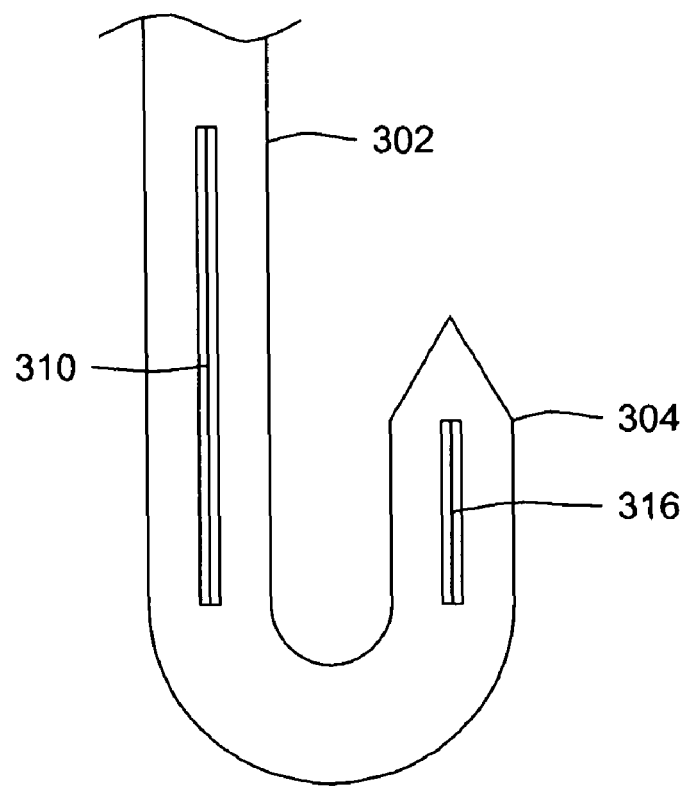
FIG. 4 is a top view of an elongate member of an intravascular device according to the invention.

FIG. 4 is a top view of an elongate member 302 of an intravascular device according to the invention. Elongate member 302 includes an anchor member 304, which may be similar to anchor members previously described or may be another suitable anchor member. Elongate member includes an inward facing edge 310 and anchor member 304 includes an inward facing edge 316. Thus, both edges should face away from the portion of elongate member 302 and anchor member 304 which are configured to contact the vessel wall. Edges 310 and 316 are susceptible to several contemplated variations. For example, in the pictured embodiment, the edges are substantially straight and are disposed on substantially straight portions of elongate member 302 and anchor member 304. In another embodiment, edges 310 and 316 may extend to join and form one continuous edge, curving between the elongate member and the anchor member. In another embodiment, there may be a third edge between edges 310 and 316, which may be disposed at a different angle and yet still away from the vessel wall. For example, this third edge may be disposed more towards the direction in which the intravascular device may be retracted. In another embodiment, this third edge may smoothly join with edges 310 and 316.

Figure 5:
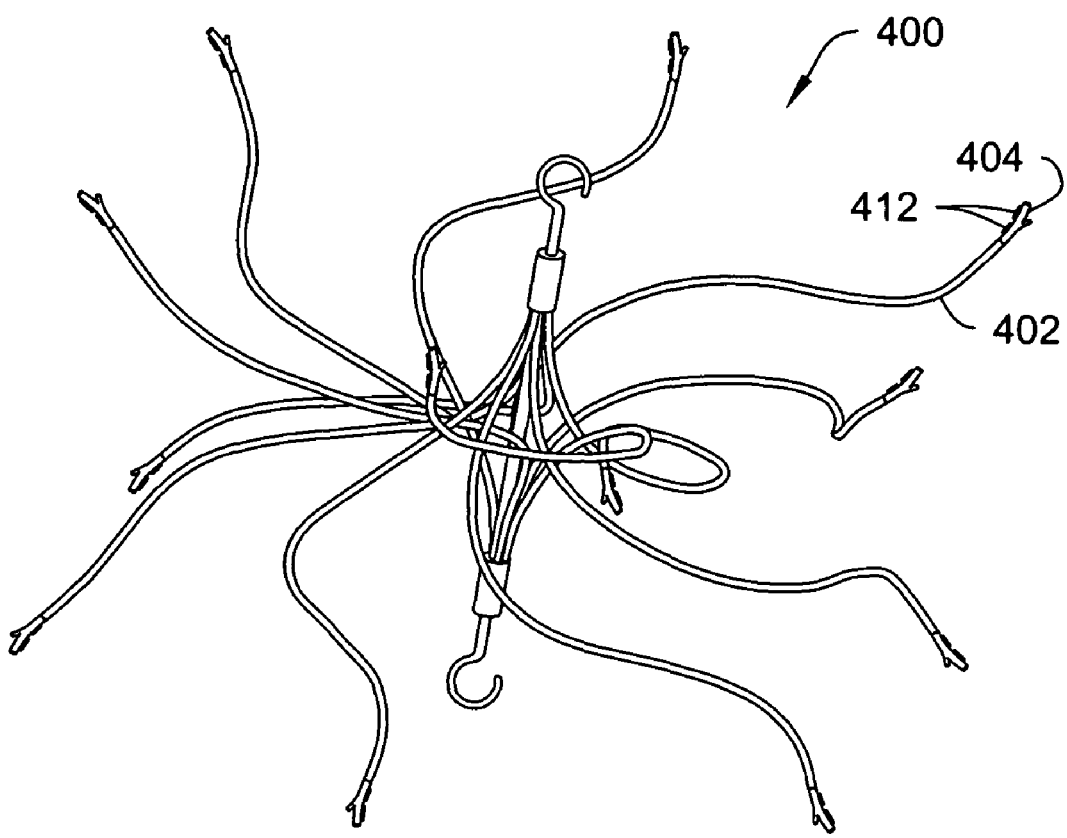
FIG. 5 is a perspective view of a vena cava filter according to the invention.
Figure 6:
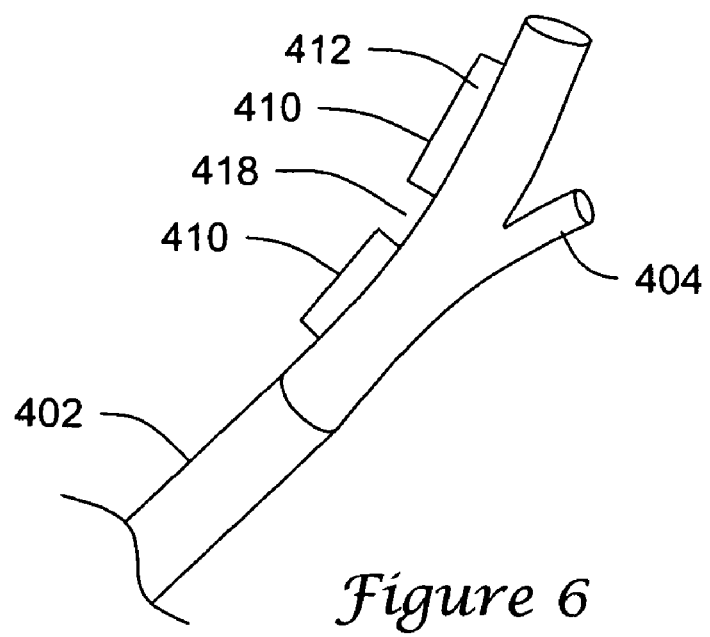
FIG. 6 is a side view of a strut of the filter of FIG. 5.

FIG. 5 is a perspective view of a thrombosis filter 400, which includes several elongate members 402 having anchoring members 404. FIG. 6 is a perspective view of an elongate member 402. Elongate member 402 includes a blade 412 having two or more separated, inward facing edges 410. Edges 410 may be separated by a break 418 in the blade. Break 418 may be a complete gap between two sections of blade 412 or may be a partial removal of material. For example, break 418 may be a v-shaped or u-shaped slot between two portions of the blade. In another embodiment, break 418 is a slight radial offset between two sections of blade 412 and may not include a longitudinal gap. Break 418 may be created by removing material during the shaping of the blade or by removing material after the blade is assembled and joined. Break 418 may also be created by assembling the blade to the elongate member in several pieces.

Other embodiments are contemplated. One example embodiment of an intravascular device has elongate members where an edge that faces generally inwards is set in a cut-out of the elongate member to reduce the overall profile, where that edge also includes one or more gaps. In another embodiment, one or more of the elongate members may be coated with a therapeutic agent, such as an anti-angiogenesis drug or other desired agent. In another embodiment, the intravascular device has elongate members with inward facing edges and anchor members configured to easily break away from the device. The embodiments herein described are only a limited selection of the contemplated embodiments and serve to illustrate the invention and show the broad applicability of the invention to many embodiments.

Figure 7:
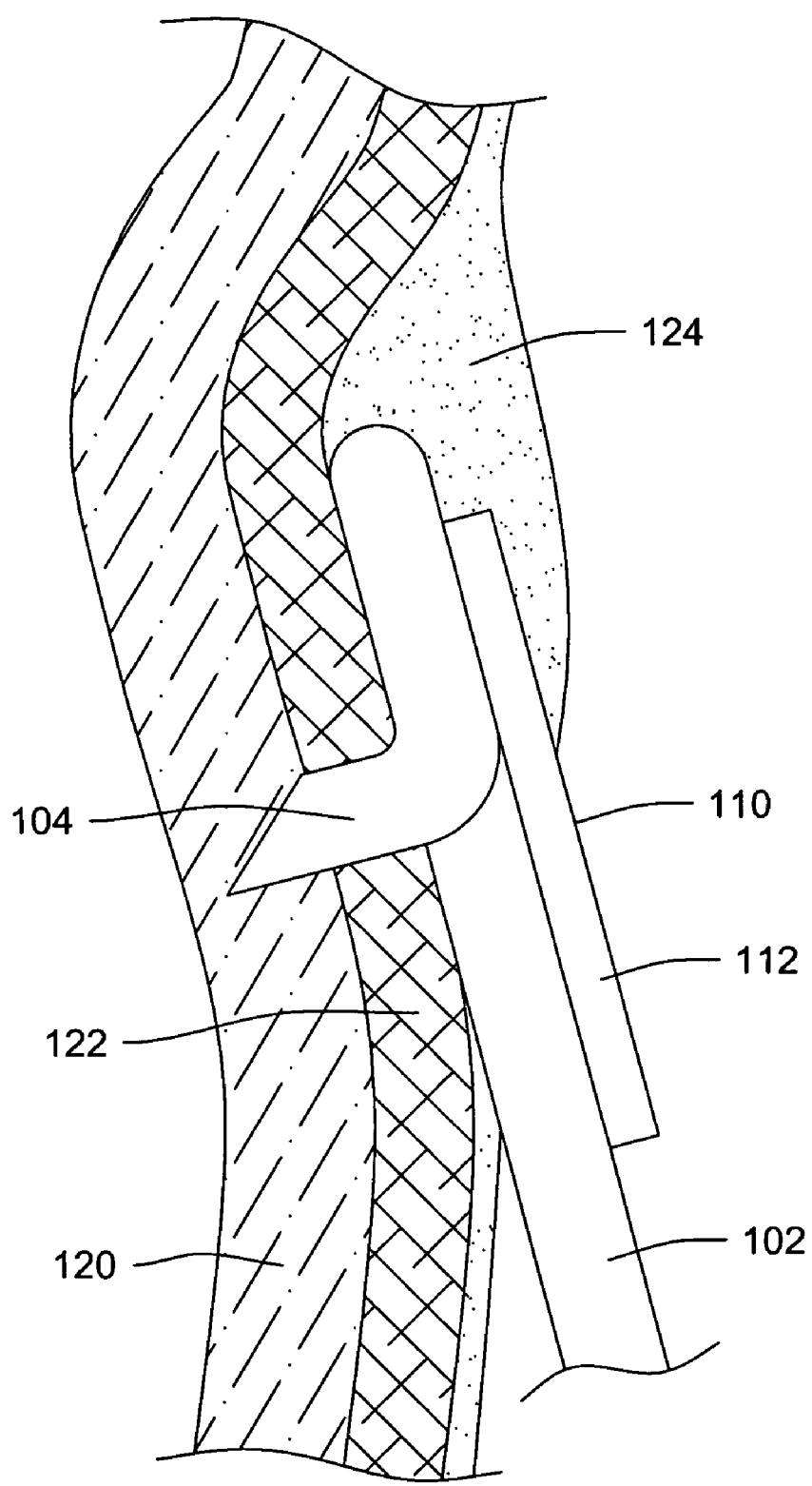
FIG. 7 is a diagrammatic view of a strut encapsulated in a vessel wall.

FIG. 7 is a diagrammatic view of a portion of elongate member 102 after vena cava filter 100 has been installed in a vena cava for a period of time sufficient for neointiminal hyperplasia to occur. Elongate member 102 includes anchor member 104 and edge 110, which edge is disposed on blade 112. The wall of the vena cava includes the adventitia 120, the media 122 and the intima 124. It is this last layer, intima 124, that encapsulates the anchor member 104 and a portion of elongate member 102. As can be seen, edge 110 faces away from the wall of the body vessel and towards the vessel centerline. Edge 110 is configured to extend beyond the portion of elongate member 102 likely to be encapsulated by intima 124 and expected neointimal hyperplasia.

When removal of vena cava filter 100 is desired, it may be accomplished by the following process, or by another suitable process. Vena cava filter 100 may be held to prevent undesired longitudinal motion, perhaps by grasping the filter with a retention device on the end of a guide wire or by other suitable method. Elongate member is urged inward. This urging may be accomplished by the action of a catheter upon the elongate member, for example. When a catheter is slid over the vena cava filter, the inner lip of the catheter end will provide a force on the elongate member that will tend to move the elongate member inwards. When the elongate member is urged inward, edge 102 may cut through intima 124, and thus provide a passage for the end of the elongate member and the anchor member through the intima. By cutting rather than tearing a passage through the intima, trauma to the vessel wall may be reduced. Trauma is reduced because a cut is generally less traumatic to tissue than a tear. Trauma is also reduced because a cut may be created using less force than a tear, and thus the surrounding tissue is subjected to less force. Also, less force needs to be delivered via the catheter. Thus, removal is possible in more situations. The urging of the elongate member may be done using one full motion, or may be done using smaller, reciprocating motions if desired. By providing a configuration where the edge extends from the intima into the vessel lumen, a spot on the vessel wall is provided where the cut may be readily started. When the intima is cut, the end portion of elongate member 102 and anchor member 104 may be readily removed from the vessel wall and the vena cava filter may then be compressed and removed.

Numerous advantages of the invention covered by this document have been set forth in the foregoing description. It will be understood, however, that this disclosure is, in many respects, only illustrative. Changes may be made in details, particularly in matters of shape, size, and arrangement of parts or order of steps without exceeding the scope of the invention. The invention's scope is, of course, defined in the language in which the appended claims are expressed.

What is claimed is:

1. An intravascular filter having a central longitudinal axis comprising:
    an elongate member;
    an anchoring member for anchoring the intravascular filter to a vessel wall attached to a distal end of the elongate member; and
    an elongate edged blade cutting member disposed along the elongate member proximate the anchoring member, wherein the edge of the edged blade generally faces towards the longitudinal central axis;
    wherein a distal end of the elongate edged blade terminates proximally of the anchoring member.

2. The filter of claim 1, wherein the elongate member comprises a first elongate section having a first end and a second end,
    wherein the second end is proximate the anchoring member, and
    wherein the cutting member extends from the first end to the second end.

3. The filter of claim 2, wherein when the filter is placed within a body vessel having a vessel wall, the filter is configured so that the anchoring member contacts the vessel wall and the first end of the first elongate section is spaced apart from the vessel wall.

4. The filter of claim 2, wherein the first elongate section and the cutting member have a first cross section,
    wherein the elongate member further comprises a second elongate section having a second cross section, the second elongate section located proximate the first end of the first elongate member, and
    wherein the first cross section has an outer extent no greater than an outer extent of the second cross section.

5. The filter of claim 2, wherein the cutting member comprises a single edge extending from the first end to the second end.

6. The filter of claim 2, wherein the cutting member comprises a first edge extending from the first end and a second edge extending from the second end.

7. The filter of claim 6, wherein the first edge and the second edge are substantially aligned.

8. The filter of claim 7, wherein the first edge is spaced apart from the second edge.

9. The filter of claim 8, wherein the cutting member further comprises a third edge disposed between and aligned with the first and second edges, the third edge spaced apart from the first and second edges.

10. The filter of claim 8, wherein the space between the first and second edges is wedge shaped.

11. The filter of claim 8, wherein the space between the first and second edges is block shaped.

12. The filter of claim 8, wherein the space between the first and second edges is u-shaped.

13. The filter of claim 1, wherein the anchoring member comprises an inwardly facing cutting member.

14. The filter of claim 1, wherein the filter is a vena cava filter.

15. The filter of claim 1, wherein the elongate member comprises metal.

16. The filter of claim 15, wherein the elongate member comprises stainless steel.

17. The filter of claim 15, wherein the elongate member comprises a nickel-titanium alloy.

18. The filter of claim 17, wherein the nickel-titanium alloy is Nitinol.

19. The filter of claim 1, further comprising a second elongate member having a second cutting member facing generally towards the longitudinal central axis of the filter.

20. The filter of claim 19, further comprising a third elongate member having a third cutting member facing generally towards the longitudinal central axis of the filter.

21. The filter of claim 1, further comprising a filtering portion for retaining emboli, the filtering portion including the elongate member.

* * * * *